(12) United States Patent
Clevenson et al.

(10) Patent No.: US 10,197,515 B2
(45) Date of Patent: Feb. 5, 2019

(54) METHODS AND APPARATUS FOR OPTICALLY DETECTING MAGNETIC RESONANCE

(71) Applicant: Massachusetts Institute of Technology, Cambridge, MA (US)

(72) Inventors: Hannah A. Clevenson, Cambridge, MA (US); Dirk Robert Englund, Brookline, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1222 days.

(21) Appl. No.: 14/325,937

(22) Filed: Jul. 8, 2014

(65) Prior Publication Data
US 2015/0192532 A1 Jul. 9, 2015

Related U.S. Application Data

(60) Provisional application No. 61/924,803, filed on Jan. 8, 2014.

(51) Int. Cl.
*G01V 3/00* (2006.01)
*G01N 24/00* (2006.01)
*G01R 33/32* (2006.01)

(52) U.S. Cl.
CPC ......... *G01N 24/006* (2013.01); *G01R 33/323* (2013.01)

(58) Field of Classification Search
CPC .................................................... G01R 33/323
USPC ......................................... 324/300, 301, 304
See application file for complete search history.

(56) References Cited

U.S. PATENT DOCUMENTS

| 5,734,766 A | 3/1998 | Flint |
| 8,547,090 B2 | 10/2013 | Lukin et al. |
| 8,885,301 B1 * | 11/2014 | Heidmann ............. G11B 5/455 360/323 |

(Continued)

FOREIGN PATENT DOCUMENTS

| WO | 2009073736 A1 | 6/2009 |
| WO | 2012/118944 A2 | 9/2012 |

(Continued)

OTHER PUBLICATIONS

Liu, C. et al., "Enhanced energy storage in chaotic optical resonators", Nature Photonics, vol. 7, May 5, 2013, pp. 473-478.

(Continued)

*Primary Examiner* — Louis Arana
(74) *Attorney, Agent, or Firm* — Smith Baluch LLP

(57) ABSTRACT

A light-trapping geometry enhances the sensitivity of strain, temperature, and/or electromagnetic field measurements using nitrogen vacancies in bulk diamond, which have exterior dimensions on the order of millimeters. In an example light-trapping geometry, a laser beam enters the bulk diamond, which may be at room temperature, through a facet or notch. The beam propagates along a path inside the bulk diamond that includes many total internal reflections off the diamond's surfaces. The NVs inside the bulk diamonds absorb the beam as it propagates. Photodetectors measure the transmitted beam or fluorescence emitted by the NVs. The resulting transmission or emission spectrum represents the NVs' quantum mechanical states, which in turn vary with temperature, magnetic field strength, electric field strength, strain/pressure, etc.

25 Claims, 9 Drawing Sheets

(56) References Cited

U.S. PATENT DOCUMENTS

| | | | |
|---|---|---|---|
| 9,157,859 B2* | 10/2015 | Walsworth | ......... G01N 21/6489 |
| 2010/0329962 A1 | 12/2010 | Twitchen et al. | |
| 2011/0309265 A1 | 12/2011 | Babinec et al. | |
| 2013/0334170 A1 | 12/2013 | Englund et al. | |
| 2014/0191139 A1 | 7/2014 | Englund | |

FOREIGN PATENT DOCUMENTS

| | | |
|---|---|---|
| WO | 2012174125 A1 | 12/2012 |
| WO | 2013/040446 A1 | 3/2013 |
| WO | 2013059404 A1 | 4/2013 |
| WO | 2013/188651 A1 | 12/2013 |
| WO | 2013/188732 A1 | 12/2013 |
| WO | 2014/011286 A2 | 1/2014 |

OTHER PUBLICATIONS

Neumann, P. et al., "Excited-state spectroscopy of single NV defects in diamond using optically detected magnetic resonance", New Journal of Physics, vol. 11, Jan. 7, 2009, pp. 1-10.

International Search Report and Written Opinion dated Oct. 16, 2014, for PCT/US14/45789, filed Jul. 8, 2014.

Abrams, Daniel et al., "Dynamic Nuclear Spin Polarization of Liquids and Gases in Contact with Nanostructured Diamond", Nano Letters, vol. 14, Apr. 22, 2014, pp. 2471-2478.

Acosta, V. M. et al., "Optical properties of the nitrogen-vacancy singlet levels in diamond", arXiv:1009.0032v3 [quant-ph] Nov. 17, 2010, pp. 1-5.

Acosta, V.M. et al., "Electromagnetically Induced Transparency in a Diamond Spin Ensemble Enables All-Optical Electromagnetic Field Sensing", Physical Review Letters, vol. 110, 213605, May 24, 2013, pp. 1-6.

Acosta, V.M., "Optical Magnetometry with Nitrogen-Vacancy Centers in Diamond", Thesis, University of California, Berkeley, 2011, pp. 1-118.

Acosta, V.M. et al., "Nitrogen-vacancy centers: Physics and applications", Materials Research Society Bulletin, vol. 38, Feb. 2013, pp. 127-130.

Budker, Dmitry, "Magnetometry With NV Ensembles in Diamond", Powerpoint Presentation, Normandy, 2012, pp. 1-39.

Chen, Edward H. et al., "Wide-Field Multispectral Super-Resolution Imaging Using Spin-Dependent Fluorescence in Nanodiamonds", Nano Letters, vol. 13, Apr. 2, 2013, pp. 2073-2077.

Clevenson, Hannah et al., "Broadband Magnetometry and Temperature Sensing with a Light Trapping Diamond Waveguide", arXiv:1406.5235v1 [quant-ph] Jun. 19, 2014, pp. 1-8.

Doherty, Marcus, W. et al., "Electronic Properties and Metrology Applications of the Diamond NV Center under Pressure", Physical Review Letters, vol. 112, 047601, Jan. 31, 2014, pp. 1-5.

Englund, Dirk et al., "Deterministic coupling of a single nitrogen vacancy center to a photonic crystal cavity", arXiv:1005.2204v1, [quant-ph] May 12, 2010, pp. 1-5.

Fan, Jonathan A. et al., "Compact Quasi-Chaotic Optical Cavity", ArXiv:physics/0508204v1, [physics.optics], Aug. 29, 2005, pp. 1-7.

Gaathon, O. et al., "Planar fabrication of arrays of ion-exfoliated single-crystal-diamond membranes with nitrogen-vacancy color centers," Optical Materials, vol. 35 (2013), pp. 361-365, Nov. 9, 2012 (available online).

Gray Cancer Institute, "Getting the best out of photodiode detectors", Advanced Technology Development Group, 2005, pp. 1-7.

Hodges, J.S. et al., "Time-keeping with electron spin states in diamond", arXiv:1109.3241v1 [physics.atom-ph], Sep. 15, 2011, pp. 1-13.

Hodges, J.S. et al., "Long-lived NV spin coherence in high-purity diamond membranes", New Journal of Physics, vol. 14, 093004, Sep. 3, 2012, pp. 1-12.

Jensen, K. et al., "Cavity-enhanced room-temperature magnetometry using absorption by nitrogen-vacancy centers in diamond", arXiv:1401-2438v1 [quantum physics], Jan. 10, 2014, pp. 1-8.

Kucsko, G. et al., "Nanometer scale quantum thermometry in a living cell", arXiv:1304.1068v1 [quant-ph], Apr. 3, 2013, pp. 1-22.

Ledbetter, M.P. et al., "Gyroscopes based on nitrogen-vacancy centers in diamond", arXiv:1205-0093v2 [physics.atom-ph], Sep. 4, 2012, pp. 1-5.

Le Sage, D. et al., "Efficient photon detection from color centers in a diamond optical waveguide", Physical Review B, vol. 85, 121202, Mar. 23, 2012, pp. 1-4.

Pham, L.M. et al., "Magnetic field imaging with nitrogen-vacancy ensembles", New Journal of Physics, vol. 13, 045021, Apr. 28, 2011, pp. 1-15.

Pham, L.M. et al., "Enhanced Metrology using preferential orientation of nitrogen-vacancy centers in diamond", Physical Review B, vol. 86, Sep. 6, 2012, 121202, pp. 1-5.

Schirhagl, Romana, et al., "Nitrogen-Vacancy Centers in Diamond: Nanoscale Sensors for Physics and Biology", Annual Reviews Phys. Chem., vol. 65, pp. 83-105, Nov. 12, 2013.

Taylor, J.M., et al., "High-sensitivity diamond magnetometer with nanoscale resolution", arXiv:0805.1367v1 [cond-mat.mes-hall], May 9, 2008, pp. 1-29.

Trusheim, Matthew E. et al., "Scalable Fabrication of High Purity Diamond Nanocrystals with Long-Spin-Coherence Nitrogen Vacancy Centers", Nano Letters, vol. 14, Nov. 7, 2013, pp. 32-36.

* cited by examiner

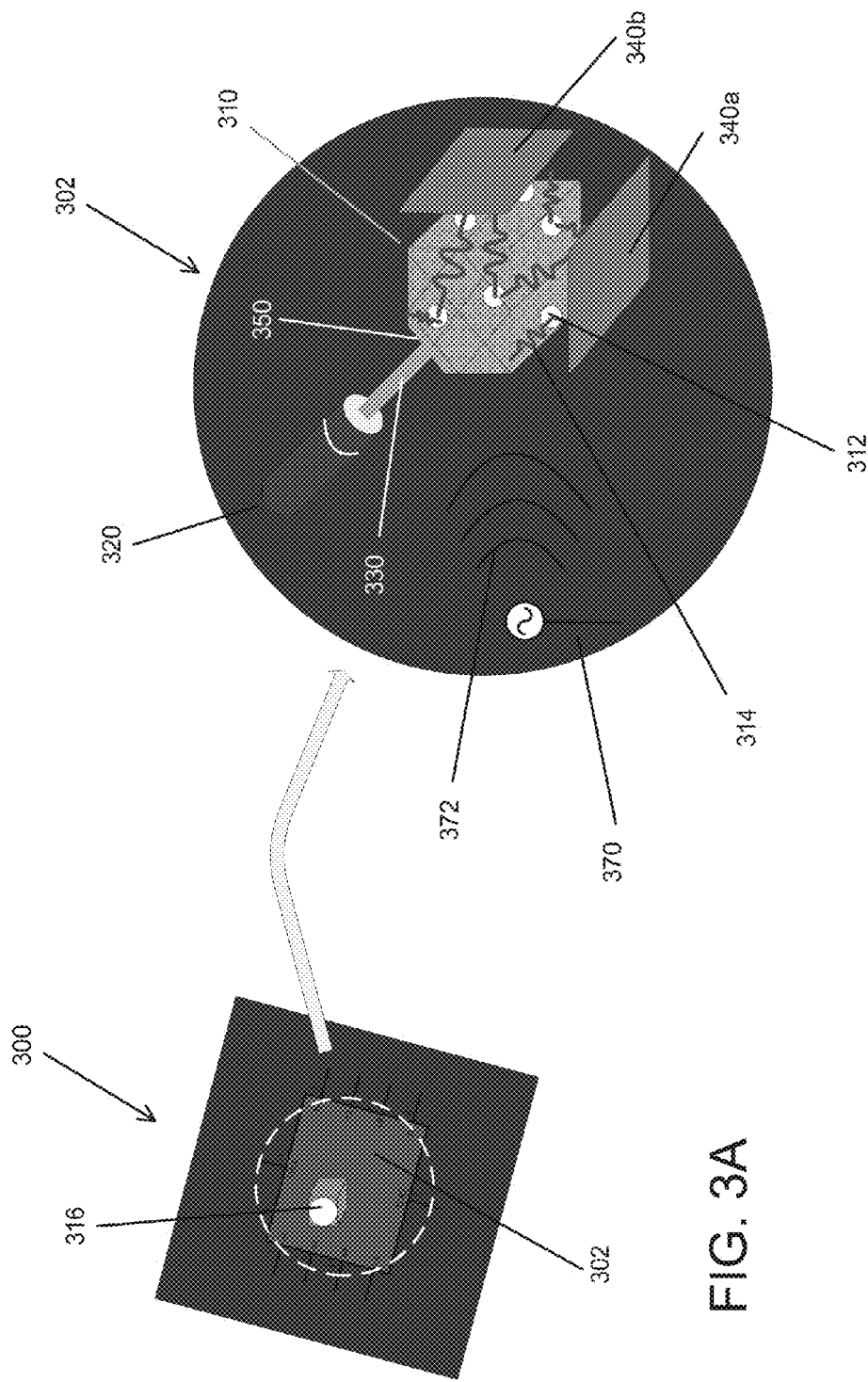

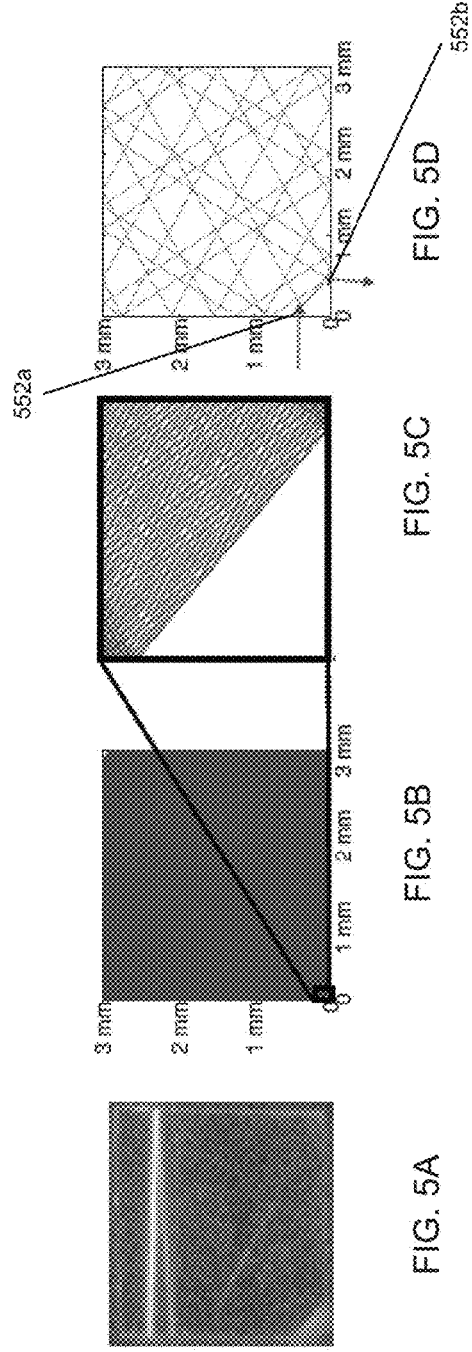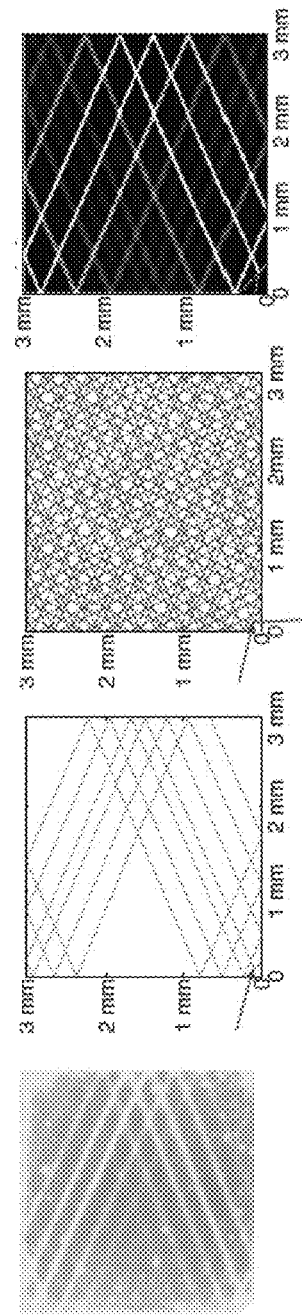

METHODS AND APPARATUS FOR OPTICALLY DETECTING MAGNETIC RESONANCE

CROSS-REFERENCE TO RELATED APPLICATION(S)

This application claims the priority benefit under 35 U.S.C. § 119(e) of U.S. Application No. 61/924,803, filed on Jan. 8, 2014, which application is incorporated herein by reference in its entirety.

GOVERNMENT SPONSORSHIP

This invention was made with government support under Contract No. N66001-13-1-4027 awarded by the Space and Naval Warfare Systems Center. The government has certain rights in the invention.

BACKGROUND

Naturally occurring materials tend to have defects in them, some of the most common types being vacancies and substitutes. In diamond crystals, a nitrogen vacancy center forms when a nitrogen atom substitutes for a missing carbon. The spin states of these defect centers exhibit long coherence times, as much as 1 s. These defect centers can also be introduced artificially, such as via irradiation. There are two charge states of nitrogen vacancy defects, a neutral nitrogen vacancy ($NV°$) and the negatively charged nitrogen vacancy (NV).

SUMMARY

Embodiments of the present invention include a method for sensing quantum mechanical spin states associated with a plurality of color centers in a room-temperature bulk crystalline material. Such a method comprises coupling an electromagnetic beam into the room-temperature bulk crystalline material along a propagation path within the room-temperature bulk crystalline material. The propagation path includes a plurality of reflections off surfaces of the room-temperature bulk crystalline material so as to cause the electromagnetic beam to excite the color centers. The reflections may be at one or more angles with respect to the surfaces of the room-temperature bulk crystalline material. The method also comprises detecting, with at least one detector, electromagnetic radiation emitted and/or transmitted by the color centers in response to the excitation of the color centers. The method also comprises determining the quantum mechanical spin states of the color centers from the detected electromagnetic radiation. Based on the quantum mechanical spin states, the amplitude of an electromagnetic field, a strain, and/or a temperature applied to the room-temperature bulk crystalline material may be determined. In some embodiments, the electromagnetic beam may be modulated.

In some embodiments, the electromagnetic beam may be coupled into the room-temperature bulk crystalline material via a facet of the room-temperature bulk crystalline material. In some of these embodiments, the divergence of the electromagnetic beam may be matched to the numerical aperture of the facet. The coupling of the electromagnetic beam into the room-temperature bulk crystalline material may cause least a portion of the electromagnetic beam to totally internally reflect off at least one surface of the room-temperature bulk crystalline material. In some embodiments, the electromagnetic beam may couple to a chaotic mode of the room-temperature bulk crystalline material, and in others, the mode may be non-chaotic.

In some embodiments, the electromagnetic radiation emitted and/or transmitted by the plurality of color centers in one or more steps of the method may be the result of the excitation of a plurality of color centers by microwave radiation.

Embodiments of the present invention also include an apparatus comprising a room-temperature bulk crystalline material containing a plurality of color centers, a light source, and at least one detector. In some embodiments, the room-temperature bulk crystalline material comprises diamond, and the color centers comprise nitrogen vacancies. The light source is in electromagnetic communication with the room-temperature bulk crystalline material and allows for an electromagnetic beam to couple into the room-temperature bulk crystalline material along a propagation path within the room-temperature bulk crystalline material. The propagation path includes a plurality of reflections off surfaces of the room-temperature bulk crystalline material so as to cause the electromagnetic beam to excite the color centers. The reflections may be at one or more angles with respect to the surfaces of the room-temperature bulk crystalline material. The detector is in electromagnetic communication with the room-temperature bulk crystalline material and detects electromagnetic radiation emitted and/or transmitted by the color centers in response to excitation of the color centers by the electromagnetic beam. In some embodiments, the apparatus further comprises a modulator that is in electromagnetic communication with the source and modulates the electromagnetic beam.

In some embodiments, the room-temperature bulk crystalline material defines a facet, and the light source is configured to couple the electromagnetic beam into the room-temperature bulk crystalline material via the facet. The divergence of the electromagnetic beam may be matched to the numerical aperture of the facet by at least one beam-shaping element that is in electromagnetic communication with the source and the facet. The source may also be configured to couple the electromagnetic beam into the room-temperature bulk crystalline material so as to cause at least a portion of the electromagnetic beam to totally internally reflect off at least one surface of the room-temperature bulk crystalline material. In some embodiments, the source is configured to couple the electromagnetic beam to a chaotic mode of the room-temperature bulk crystalline material, and in others to non-chaotic modes.

In some embodiments, the apparatus further comprises a microwave source that is in electromagnetic communication with the room-temperature bulk crystalline material. The microwave source excites the plurality of color centers with microwave radiation so as to cause the color centers to emit and/or transmit the electromagnetic radiation. In some embodiments, the apparatus further comprises a processor that is operably coupled to the detector(s) and determines the quantum mechanical spin states of the plurality of color centers based at least in part on the electromagnetic radiation detected by the detector(s). In some of these embodiments, the processor is configured to determine a strain, a temperature, and/or an electromagnetic field applied to the room-temperature bulk crystalline material based at least in part on the determined quantum mechanical spin states of the color centers.

Further inventive embodiments of the present invention include a sensor comprising a diamond, a laser, and at least one detector. The diamond defines a plurality of polished surfaces and comprises a plurality of nitrogen vacancies, each of which has a first energy level and a second energy level. The laser may be in optical communication with the diamond. In operation, the laser emits a laser beam that is coupled into the diamond so as to excite at least some of the color centers along a propagation path within the diamond. The propagation path comprises at least one total internal reflection from at least one polished surface of the plurality of polished surfaces. The detector is in optical communication with the diamond and detects a change in optical radiation emitted and/or transmitted by the excited color centers. In such embodiments, the change in optical radiation is proportional to a change in temperature, pressure, and/or electromagnetic field applied to the diamond.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 3A and 3B show a conveniently packaged, on-chip laser diode-based sensor comprising an excitation laser, a bulk material comprising a plurality of color centers, a microwave antenna, and at least one photodetector.

FIGS. 5A and 5E show optical images of fluorescence from a single-pass and light-trapping excitation geometries, respectively, in a bulk diamond crystal containing multiple nitrogen vacancies.

FIGS. 5B-5D and 5F-5H show numerically simulated laser reflection patterns inside a faceted diamond sample.

DETAILED DESCRIPTION

Figure 1:
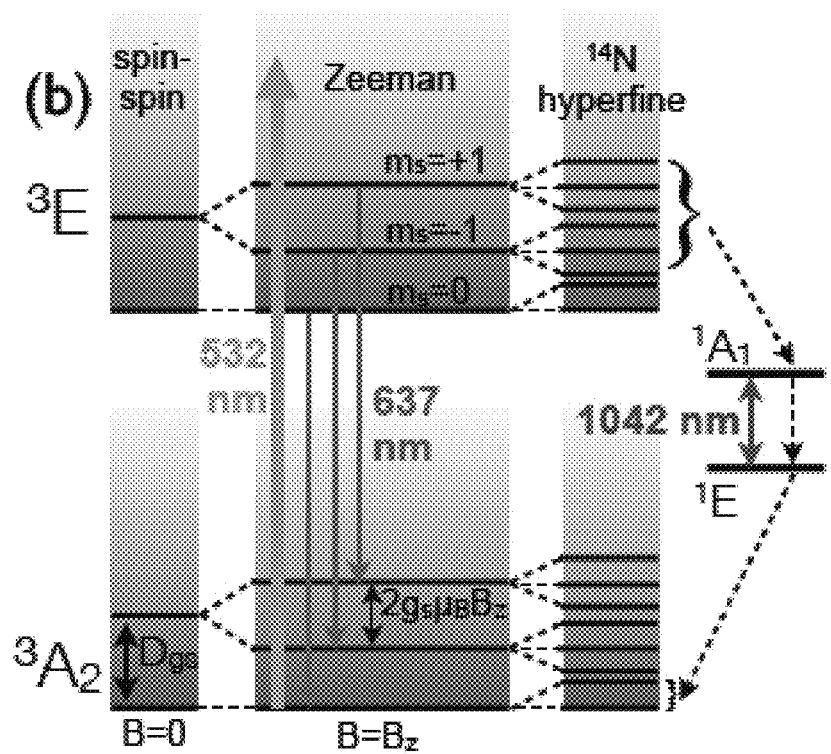
FIG. 1 shows an energy level diagram of nitrogen vacancy centers in bulk diamond.

Spin systems comprising color centers in diamond, such as the negatively charged nitrogen-vacancy (NV) centers in combination with other neighboring spins, promise a new era of spintronic devices. Harnessing the quantum behavior of solid-state systems such as these nitrogen vacancies may give rise to all-solid-state solution to quantum information processing, communication, and sensing. Examples of quantum sensing applications include thermometry, magnetometry, electric field sensing, pressure sensing, inertial sensing, and/or timekeeping. Those applications may exploit the ability of the NV to be initialized and read out optically, as well as utilize continuous-wave (CW) approaches and/or pulsed protocols. As experiments progress from studying single color centers to addressing spin chains, grids and ensembles, traditional state preparation and readout through confocal microscopy may pose limitations. For example, although high resolution measurements can be obtained using single NV centers on a confocal microscope setup, in some embodiments, addressing a large number (N) of NV centers can enhance the sensitivity by as much as $\sqrt{N}$. However, both efficiently exciting and collecting signal from large ensembles of NVs may pose a challenge. For example, green laser excitation may be inefficient due to the low NV absorption cross section, which can result in meter-long absorption path lengths for moderate NV densities of $10^{15}$ to $10^{17}$ cm$^{-3}$.

NV ensemble-based sensing may be limited by low excitation conversion efficiencies and ensembles sizes of nitrogen vacancies. Wide-field charge coupled device (CCD) cameras can be used to address small numbers of NV centers (e.g., up to several hundred). Fabry-Perot cavities may increase the optical depth of the infrared resonant transition, and the technique may be expanded to the excitation laser. However, cavities may require precise alignment combined with stabilized, narrow-linewidth excitation lasers. For example, a cavity-based path length of 1 m in a mm-scale device suggests a finesse F~1000, resulting in a cavity linewidth of $c/2n_dL$~62 MHz, where c is the speed of light, $n_d$ is the index of refraction of diamond, and L is the length of the cavity. This cavity linewidth may limit the timescale of the state preparation and readout pulses to >16 ns, with greater restriction at higher finesse.

Some devices may address NVs in bulk diamond either with a single pass through the bulk crystal or with several bounces back and forth, utilizing silver or dielectric mirror coatings on the edges. However, in addition to aforementioned cavity limitations, it can be difficult to adhere silver or dielectric coatings directly on the edges of the micron-width bulk diamond. Further, efficient collection can be done in a single-pass geometry, but excitation is limited by the low optical depth. As such, it may be desirable to increase the number of NVs that interact with the laser beam, which can be done by highly irradiating and annealing samples to increase the NV density. Increasing the density of NV centers too much, however, can reduce the spin coherence times.

Color centers may also emit and/or transmit electromagnetic radiation in response to excitation by a microwave source. For instance, a microwave source may manipulate the color centers so as to change their quantum mechanical spin state. The manipulation of the quantum mechanical spin states of the color centers may be accomplished through control sequences. For example, the control sequences may comprise continuous-wave optically detected magnetic resonance, Ramsey sequences ($\pi/2$, $\pi/2$), Hahn echo sequences ($\pi/2$, $\tau$, $\pi$), Carr-Purcell-Meiboom-Gill (CPMG) sequences ($\pi/2$, $\tau$, $\pi$, $\tau$, $\tau$, $\pi$), pulse wave sequences (e.g., $\pi/4$, $\pi/4$), etc., where $\tau$ is delay time, a $\pi/4$ pulse changes orients the color centers' spin states, a $\pi/2$ pulse places the spin vectors of the spin states into a transverse direction, and a $\pi$ pulse flips the vector direction. The frequency, amplitude and/or phase of these sequences may all be controlled, with the primary frequency in the range of 1-4 GHz, and the amplitudes in the −20 to +50 dBm range.

In some embodiments, the color centers in diamond may comprise carbon vacancy defects replaced with extrinsic materials, such as silicon, sulfur, nickel, cobalt, etc. For example, a silicon atom may take the place of a missing carbon atom to form a negatively charged silicon vacancy color center. In other examples, carbon vacancy defects may be replaced by sulfur, nickel, or cobalt to form, respectively, sulfur-, nickel-, or cobalt-vacancy color centers. In some of these embodiments, for example in the case of nickel, two carbon atoms may be missing and a single nickel atom may be situated in between the sites of the missing carbon atoms.

FIG. 1 shows an energy-level diagram of a diamond NV center with radiative transitions (solid lines) and non-radiative transitions (dotted lines). The energy degeneracy between states in the ground state triplet sublevels $^3A_2$ with different z axis spin projection values $m_s=\pm 1$ may be lifted by applying a static magnetic field and tuning the microwave excitation to resonantly drive the $m_s=0$ to $m_s=\pm 1$ spin transitions, causing a drop in observed fluorescence. Without being bound by any particular theory, the energy of $^3A_2$ in the weak field, low strain approximation comprises the term $D_{gs}S_z^2$ where $D_{gs}$ is the ground state crystal field splitting, and $S_z$ is the spin projection onto the z axis.

Because $D_{gs}$ depends on quantities including but not limited to temperature, crystal strain, external electric fields, and external magnetic fields, shifts in the observed optically detected magnetic resonance (ODMR) spectrum (and in the fluorescence) can be attributed to quantities that affect the value of $D_{gs}$. As a result, it is possible to measure the temperature, crystal strain, external electric field, and/or external magnetic field applied to a diamond NV center by measuring the ODMR spectrum and/or the emitted fluorescence. The ODMR spectra may be obtained from fluorescence measurements which may be done by monitoring the 637 nm transition from the triplet excited state ($^3E$) to the triplet ground state ($^3A_2$), while optical transmission measurements may be done by using the 1042 nm transition in the metastable singlet state ($^1A_1$). For other materials with other defect centers (e.g., silicon carbide crystals), light with different wavelengths may be used based on the material's energy levels.

Figure 2:
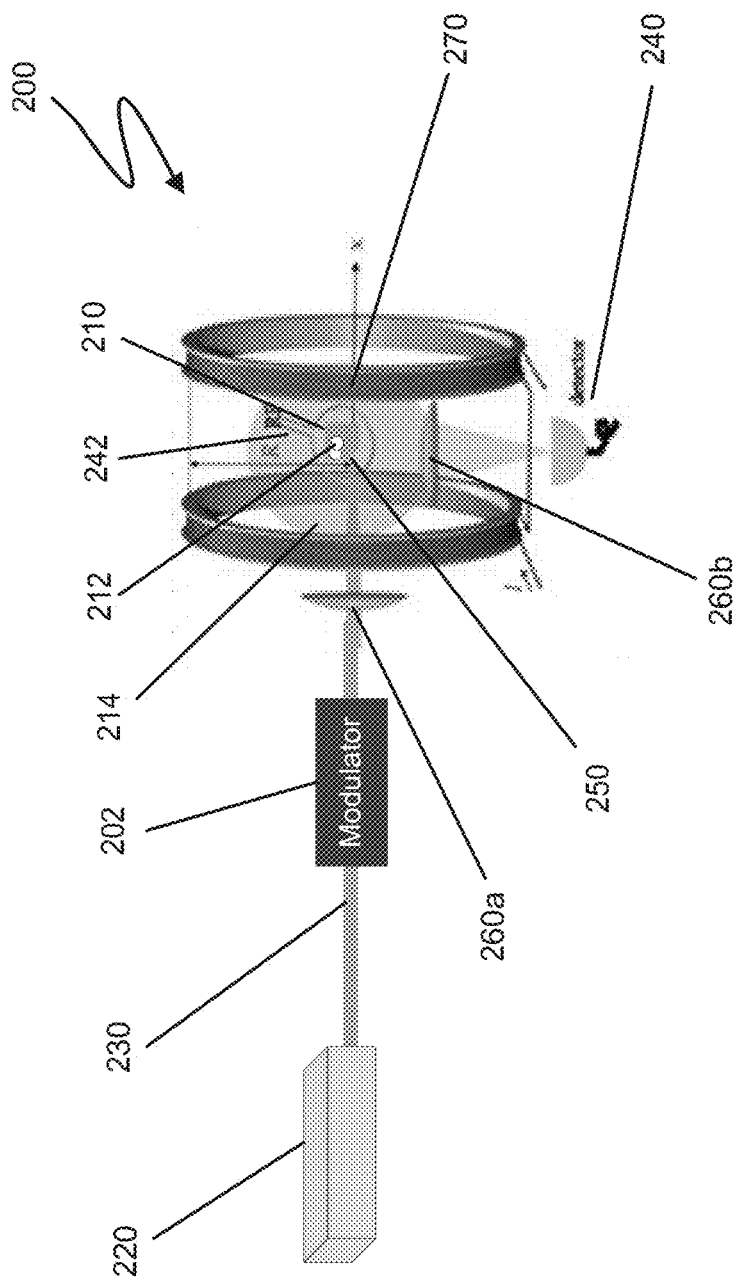
FIG. 2 shows a bulk material sensor based on light trapping in a diamond or other crystal with multiple nitrogen vacancies or other color centers.

FIG. 2 shows an exemplary sensing apparatus 200 that monitors temperature, strain, and/or electromagnetic field using color centers 212 (e.g., NV centers) in a bulk material 210 (e.g., diamond, silicon carbide, etc.). The bulk material 210 may be a crystal or non-crystalline material that is transparent to some or all fluorescence that may be emitted by the plurality of defect centers in the material. It may also have a high-refractive index, and/or have dimensions that are significantly larger than the relevant wavelength of light, such as the laser beam 230.

The sensor 200 includes an excitation laser 230 that emits an laser beam 230. In some embodiments, the light source 220 may emit the laser beam 230 at wavelengths from about 450 nm to about 650 nm, and in particular at wavelengths of 532 nm, 575 nm, and 637 nm. Throughout the instant specification, the term "green" may be used to characterize wavelengths in the range of from about 450 nm to about 650 nm, and in some embodiments, a specific wavelength and/or ranges of wavelengths may be given as needed to illustrate specific aspects of the embodiments. For example, the laser beam may be a spatially filtered 532 nm wavelength beam from a Verdi V5 light source.

The sensor 200 may include a modulator 202, such as but not limited to an acousto-optical modulator (AOM), chopper wheel, or any other suitable modulator, that modulates the laser beam 230 as shown in FIG. 2. For instance, the modulator 202 may act as a gate that selectively blocks and unblocks the laser beam 230, e.g., to prevent the laser beam 230 from propagating towards the bulk material 210. The modulator 202 may also modulate the amplitude and/or the phase of the laser beam 230.

The sensor 200 can also include one or more beam-shaping elements placed in proximity to the bulk material 210 to collect and focus beams entering and/or leaving the bulk material. In this example, a lens 260a is located along the path of the excitation laser beam 230 coming through the modulator 202. The lens 260a may have a numerical aperture selected to match numerical aperture of a facet or notch 250 in the bulk material 210. The beam 230 propagates inside the bulk material 210 along a path that involves reflections at one or more angles with respect to the bulk material's surfaces. These reflections may be total internal reflections and/or reflections off coatings applied to the bulk material's surfaces. Thanks to these reflections, the bulk material 210 acts as a light-trapping waveguide that guides the laser beam 230 along a propagation path that be much longer (e.g., several orders of magnitude longer) than the bulk material's length or width.

The bulk material 210 may be located in a multi-axis Helmholtz coil setup 270 (only one axis is shown here for clarity), which may be used, for example, to apply a uniform static or a slowly varying magnetic field to one or more of the color centers 212 in the bulk material 219. For example, the set up may comprise three sets of mutually perpendicular Helmholtz coils that range in diameter from about 8 inches to about 12 inches. In some embodiments, the magnetic field may be applied using permanent magnets.

In this example, the sensor 200 also includes a radio-frequency (RF) source, shown in FIG. 2 as an impedance-matched single-loop antenna 242, that can be used to deliver microwave excitation to the color centers 212. The RF antenna 242 may also be placed in electromagnetic communication with the bulk material 210, e.g., approximately 1-2.5 mm above the bulk material. In this case, the RF antenna 242, which may be coupled to an RF signal generator (not shown), acts as a microwave source that can apply continuous-wave or frequency-swept microwave excitation to the color centers 212 in the bulk material 210. For example, in some embodiments, the RF signal may be swept from about 2.1 GHz to about 3.1 GHz. In some embodiments, the resonances may be split out further (e.g., due to larger magnetic fields), and the RF signal may to be swept even further. When a lock-in amplifier is used to detect the resonance(s), the RF signal may be modulated at 1.5 kHz with a modulation depth of 1 MHz. In some embodiments, the RF antenna 242 may act as a microwave source that can apply pulses of microwave radiation to the color centers 212 of the bulk material 210.

In operation, the laser beam 230, Helmholtz coil 270, and RF source 242 excite all or nearly all of the color centers 212 in the bulk material 210. As a result, the color centers 212 absorb the incident light and may in some instances fluoresce, producing an optical output proportional to any strain, temperature, electric field, and/or magnetic field applied to the color centers 212 in bulk material 210. One or more condenser lenses 260b and/or other optical elements may be used to collect the transmitted light and/or fluorescence emitted by the color centers 212 in response to excitation by the laser beam 230. Emitted fluorescence may be directed through an optional bandpass filter (not shown) that transmits the fluorescence emitted by the NV defect centers 212 and reflects or attenuates light at other wavelengths, including light emitted by the laser 220. The photodetector(s) 240, which may be amplified silicon diode photodetectors or other suitable detectors, produce photocurrent or other electrical signals representative of the transmitted light and/or fluorescence, which in turn varies with changes in strain, temperature, electric field, and/or magnetic field applied to the color centers 212 in bulk material 210. These electrical signals can be demodulated and processed using a lock-in amplifier (e.g., a Stanford Research System SRS-850) or other suitable electronics.

FIGS. 3A and 3B show an on-chip sensor 300 that includes a bulk material 310 (e.g., diamond) containing multiple color centers 312 (e.g., NVs) and a diode laser 320 formed on a substrate 302. A microwave source, shown here as a microwave antenna 370, and photodetectors 340 may also be packaged on or with the substrate 302. This design and packaging allows for the sensor 300 to be used for portable, precision measurement of magnetic fields, electric fields, temperature, and pressure/strain (e.g., through a connection piece 316).

The sensor 300 can operate over a very broad range of temperatures, from exceedingly low cryogenic temperatures to very high temperatures in harsh environments. For example, the sensor 300 can operate at room temperature (e.g., at about 273 K to about 300 K), at cryogenic temperatures (e.g., below about 150 K, which includes both liquid nitrogen cooled temperatures (to about 77 K) and liquid helium cooled temperatures (to about 4 K)), and high temperatures (e.g., temperatures exceeding about 700 K). For example, a sensor 300 with bulk diamond 310 at room temperature (e.g., about 25° C.) may be used for measuring magnetic fields, electric fields, temperature, pressure/strain, rotation, and/or time.

In operation, the diode laser 320 emits a laser beam 330 at a wavelength of about a 532 nm towards a notched corner (facet) 350 of the bulk diamond crystal 310, which may be at room temperature (e.g., about 25° C.). As described above, the laser beam 330 propagates along a path within the crystal 310 that involves multiple total internal reflections (e.g., tens to thousands of reflections) off the crystal's surfaces. Put differently, the crystal 310 "traps" the laser beam 330 due to the propagation geometry and the index mismatch between the crystal 310 and the surrounding media (e.g., air). This light-trapping geometry results in a much longer propagation path length within the crystal 310, which in turn yields a much higher likelihood that most, if not all, of the color centers 312 will absorb at least a portion of the laser beam 330. In some cases, the color centers 312 may absorb all or substantially all of the laser beam 330.

The antenna 370 may be used to provide microwave excitation 372 to the bulk crystal 370. For instance, the antenna 370 may emit a Hahn echo sequence, Ramsey sequence, or any other suitable sequences of microwave pulses. And a static or slowly varying magnetic field may be provided at the diamond crystal by multi axis (e.g., three mutually perpendicular axis) Helmholtz coils (not shown) or any other suitable magnetic field source.

The color centers 312 in the bulk material 310 absorb the incident light and my emit fluorescence 314 at a wavelength in the range of about 600 nm to about 800 nm (broadly referred hereinafter as "red"). The color centers 312 may emit this radiation approximately isotropically from the bulk crystal 310, with each surface of the bulk crystal 310 emitting about $\frac{1}{6}^{th}$ of the total emitted signal. The emitted fluorescence may be collected using one or more photodiodes 340 (e.g., 340a faces one surface of a the bulk crystal, 340b faces another surface, etc.) located in proximity from the diamond crystal. If desired, the sensor 300 may include one or more lenses (not shown) to increase the collection efficiency of the red fluorescence. In some embodiments, up to 20% of the emitted red fluorescence may be collected with the sensor.

The measured fluorescence can be used to determine quantities such as but not limited to magnetic fields, electric fields, temperature, pressure/strain, frequency instability, rate of rotation, etc., as discussed in detail with reference to FIG. 8. Furthermore, one may also be able to estimate the number of NVs addressed in the bulk crystal from the collected fluorescence. For example, from determinations and/or estimations of approximate number of NV centers in a diamond crystal, the number of photons emitted by excited NVs per second, and the collection efficiency of the sensor, one may calculate the approximate number of defect centers addressed by the laser beam based on the collected fluorescence. This number of addressed defect centers may increase with increased input power and/or for smaller devices.

Figure 4A:
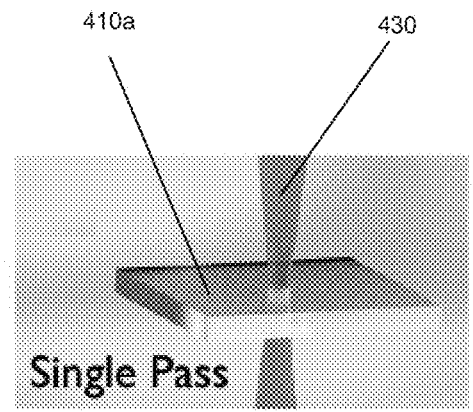
FIG. 4A shows single-pass geometry for exciting color centers in a bulk material.
Figure 4B:
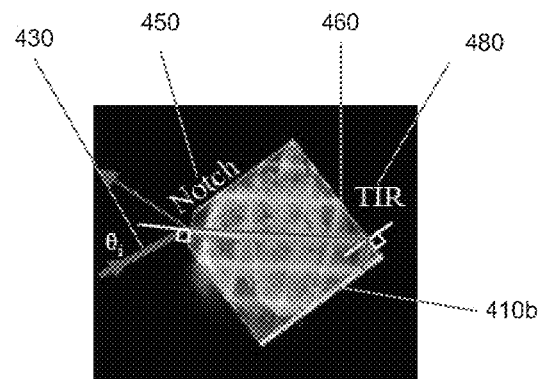
FIG. 4B shows a light-trapping geometry exciting color centers in a bulk material with a prism-like input facet (notch) in one corner.

FIGS. 4A and 4B show excitations of color centers in a crystal using a single pass beam transmission approach and a light-trapping waveguide geometry, respectively. FIG. 4A shows the single pass beam transmission of a green excitation laser 430 traveling through a bulk diamond crystal 410a in one pass. In such embodiments, the laser beam can address at most the number of NV centers that are along the path of the single pass laser beam, and as such the absorption of the laser beam may be low.

Nevertheless, one may use single-pass beam transmissions to estimate the number of NV centers in a bulk crystal. For example, one may measure absorption constants of bulk materials from single pass beam transmissions, which for a diamond crystal of size 3 mm$^2$ by 300 μm is about $\alpha \approx 0.45$ cm$^{-1}$, obtained after accounting for front and back surface reflections. Such a volume of diamond crystal corresponds to about $4.76 \times 10^{20}$ carbon atoms with no defects, and from these parameters, one may estimate NV center density of 1 part per million (1 ppm), approximately $10^{14}$ NV centers in each one of the four orientations in a diamond crystal.

FIG. 4B shows coupling of an laser beam 430 into a bulk diamond 410b at a facet (notch) 450 in one corner, also called a light-trapping diamond waveguide (LTDW). The input angle and size of the facet 450 may be chosen to allow for a propagation path 480 that includes a large number of reflections 460 (e.g., 10-10,000) within the LTDW. To avoid polishing imperfections and scattering at corners of the bulk crystal 410b that might attenuate the beam, the coupling (input) angle may be selected such that propagation path lies mainly within the interior of the bulk crystal 410b.

Since beam paths that couple into the notch 450 may also couple out of the bulk diamond 410b, a smaller notch may confine the light more effectively than a larger notch. However, a larger facet may allow for entrance angles and propagation paths 480 in which the reflected beam is more likely to satisfy the total internal reflection (TIR) condition, which occurs at reflections $\theta > \theta_c = 24.6°$ for diamond in air. This can result in more uniform excitation of the color centers 412 inside the crystal 410b. Further, using TIR this may make it possible to achieve long propagation paths 480 without applying metallic and/or layered insulator reflective coatings to the bulk crystal's surfaces.

The facet angle may also be selected based on a particular coupling geometry or desired propagation path 480. For example, one may utilize a prism-like input facet 450 at a desired angle (e.g., 45°) relative to the other surfaces of the LTDW, allowing light to couple into the structure through the facet while being confined by TIR on the other surfaces, resulting in multiple overlapping reflections within the LTDW and allowing the laser beam to address a large number of NV centers. For example, the prism-like input facet 450 may be at about 45° relative to the other surfaces of the LTDW, and light may be coupled to the structure through this facet. In some embodiments, other angles may be used, and some angles may lead to longer beam path lengths than others.

The laser beam's Rayleigh range, which is defined as the beam's waist size divided by its numerical aperture, also affects how many NVs can be addressed. In general, the Rayleigh range should be of the same order of magnitude as the length of the propagation path to prevent the beam from diverging too quickly (or too slowly). Put differently, the beam should be focused to a point at the end of the propagation path.

Figure 4C:
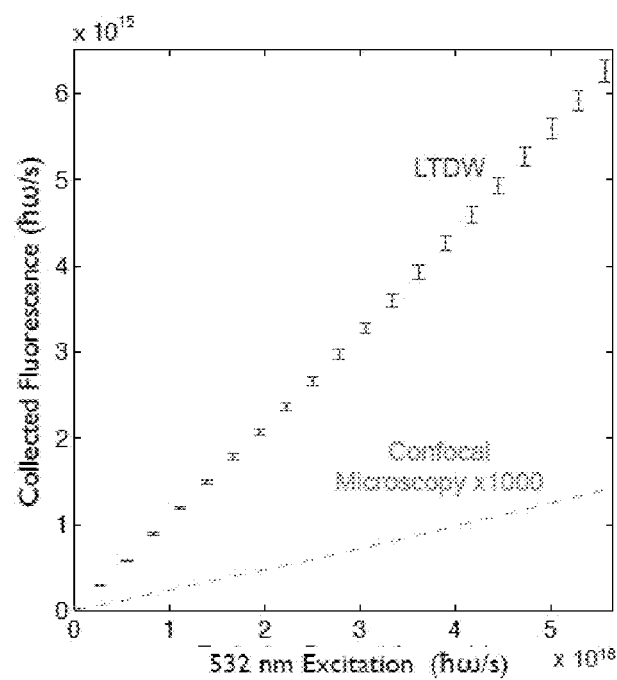
FIG. 4C shows a plot of collected fluorescence versus excitation strength of the single-pass geometry shown in FIG. 4A (dashed line) and light-trapping geometry shown in FIG. 4B (dots with error bars).

FIG. 4C shows a plot of collected fluorescence measurements versus excitation strength of single pass transmission excitation (lower curve), discussed with reference to FIG. 4A, and LTDW excitations (upper curve), discussed with reference to FIG. 4B, in bulk diamond crystal for a 532 nm wavelength laser beam. The bulk diamond crystals in both measurements have same absorption constant of $\alpha \approx 0.45$ cm$^{-1}$. The upper curve of FIG. 4C shows for every 960 excitation photons that enter the LTDW, one photon of red fluorescence gets collected in a fluorescence measurement. Adjusting for collection efficiency of approximately 20%, this gives conversion efficiency of about 2.15%, i.e., about 1 red photon is emitted for every about 48 green photons that enter the LTDW. This conversion is a factor of about $2.3 \times 10^3$ better than the approximately 4.2% collection efficiency for fluorescence measurements made in a single pass transmission geometry using a solid immersion lens and confocal setup. This calculation does not take into account expected scattering losses due to polishing imperfections and/or debris on the surface of the diamond, which may further increase the conversion efficiency.

Some or all of the increased collected fluorescence of the LTDW, as compared to the single pass approach, may be ascribed to the greatly extended path length of the excitation laser that excites larger ensembles of NV centers with comparable input laser power. For example, by coupling to broad-band, non-chaotic modes, the optical path length of the laser beam in the LTDW may be up to $10^5$ longer than the optical path length in a typical single-pass geometry, leading to close to 100% absorption of the laser beam 430 that enters the diamond crystal 410b.

In some embodiments, the laser beam 430 may couple to a chaotic mode supported by the bulk crystal 410b. For example, the laser beam 430 may propagate along an unpredictable, non-repeating path within the crystal 410b (e.g., like the non-repeating path(s) supported by a stadium resonators). Even though a chaotic mode may involve propagation along a non-repeating path, coupling to chaotic modes is useful for addressing some or all of the color centers in the crystal 410b in an even manner. In some embodiments, the LTDW may achieve a propagation path length of up to about 30 meters, allowing for an energy conversion enhancement of approximately $10^5$ or more over single-pass schemes. This may be particularly useful for light trapping in diamonds with lower NV densities.

In some embodiments, for the same excitation power, the increase in the number of NVs addressed by an laser beam in LTDWs is proportional to the optical path lengths. The LTDW geometry allows for efficient conversion of excitation photons into fluorescence signal in ODMR of an ensemble of NVs in diamond, with a collection efficiency of about 20%. Simultaneously efficient excitation light absorption and fluorescence collection allow for a conversion efficiency from green excitation to collected fluorescence in excess of 2%.

Furthermore, increasing the excitation laser power may allow for both higher excitation rates of previously addressed NVs, and path length extension of the beam in the device to address more NVs. Depending on the input angle and input facet size, TIR beam excitation patterns can be tuned so that a large part or the entirety of the LTDW and some or all the NVs therein are addressed. As the excitation laser power is increased, fluorescence increases linearly, indicating operation in a regime that is far below saturation. For nearly or fully perfect TIR, negligible scattering loss at the diamond surfaces, and using the measured absorption constant (e.g., $\alpha \approx 0.45$ cm$^{-1}$ for the diamond crystal discussed above), it may be shown that approximately 99% of the input laser beam may be absorbed over a path length of 15 cm, in contrast to the low absorption of the single pass approach. In some embodiments, a beam may not exit the sample, indicating the full absorption of the laser beam into the LTDW.

FIGS. 5A-5H show simulated as well as optical images of single-pass beam transmissions and LTDW laser beam reflection patterns in a 3 mm$^2$ by 300 μm diamond crystal. The crystal size may be determined by balancing the desire to avoid scattering losses with the desire for better spatial resolution. In smaller crystals, the beam may reflect off of edges more often for a given path length, which could result in more scattering losses if there are imperfections in the crystal's surface. In a larger structure, longer path lengths could be possible, but once most or the entire excitation beam is absorbed, the remaining path length may not contribute to further absorption. However, the larger structures may provide measurements with poorer spatial resolution. FIG. 5A shows an optical image of fluorescence of a single pass excitation in a diamond crystal, discussed in detail with reference to FIG. 4A. A large portion of the image of the crystal is missing marks of fluorescence, showing that in a single pass excitation, a large number of the NV centers may not be addressed by the laser beam, and absorption of the beam by the NV centers is low. FIG. 5B shows a result of a numerical analysis of a laser beam propagation path that results in a 31.5 meter path length in the LTDW. This long path length corresponds to a 35.8° angle of incidence (measured from a line perpendicular to the notch facet) and a 150 µm notch length.

The entrance angle and position to achieve the longest propagation path length in the LTDW may depend heavily on the length of the notch. For example, although facets with sizes about 50 µm and smaller work well in simulations, in practice the focal spot of the excitation laser may start imposing constraints. Furthermore, for situations where the recovery of the beam after some number of reflections inside the LTDW is desired, larger facets may be better suited. For example, for transmission measurements, a shorter path length may maintain the beam profile for more efficient collection. An example of such situation where a beam enters an LTDW at a point 552*a* in the notch, reflects multiple times (e.g., 32 times in the simulation shown in FIG. 5D) and exits at a different point 552*b* on the notch is shown in FIG. 5D. Such embodiments allow for spatial separation between the excitation laser and the detector in transmission measurements.

FIGS. 5F and 5G show numerical simulations corresponding to laser beam reflection patterns in the LTDW shown in the fluorescence optical image of FIG. 5E. The optical image is taken through a 600 nm long-pass filter, and shows only about 20 visible reflections in line with the simulation results in FIG. 5F, where the same notch facet length, entrance angle and position is used and the simulation is limited to about 20 reflections. However, allowing the simulation to run to completion shows further TIR patterns that emerge and are comparatively too dim to be visible on the optical image of FIG. 5E. In principle, increasing the laser power until saturation behavior of the NVs is observed may allow for the full path length in the LTDW to be uniformly excited. In some samples of LTDW, saturation may not be observed even for laser power of about 5 Watts.

Figure 6:
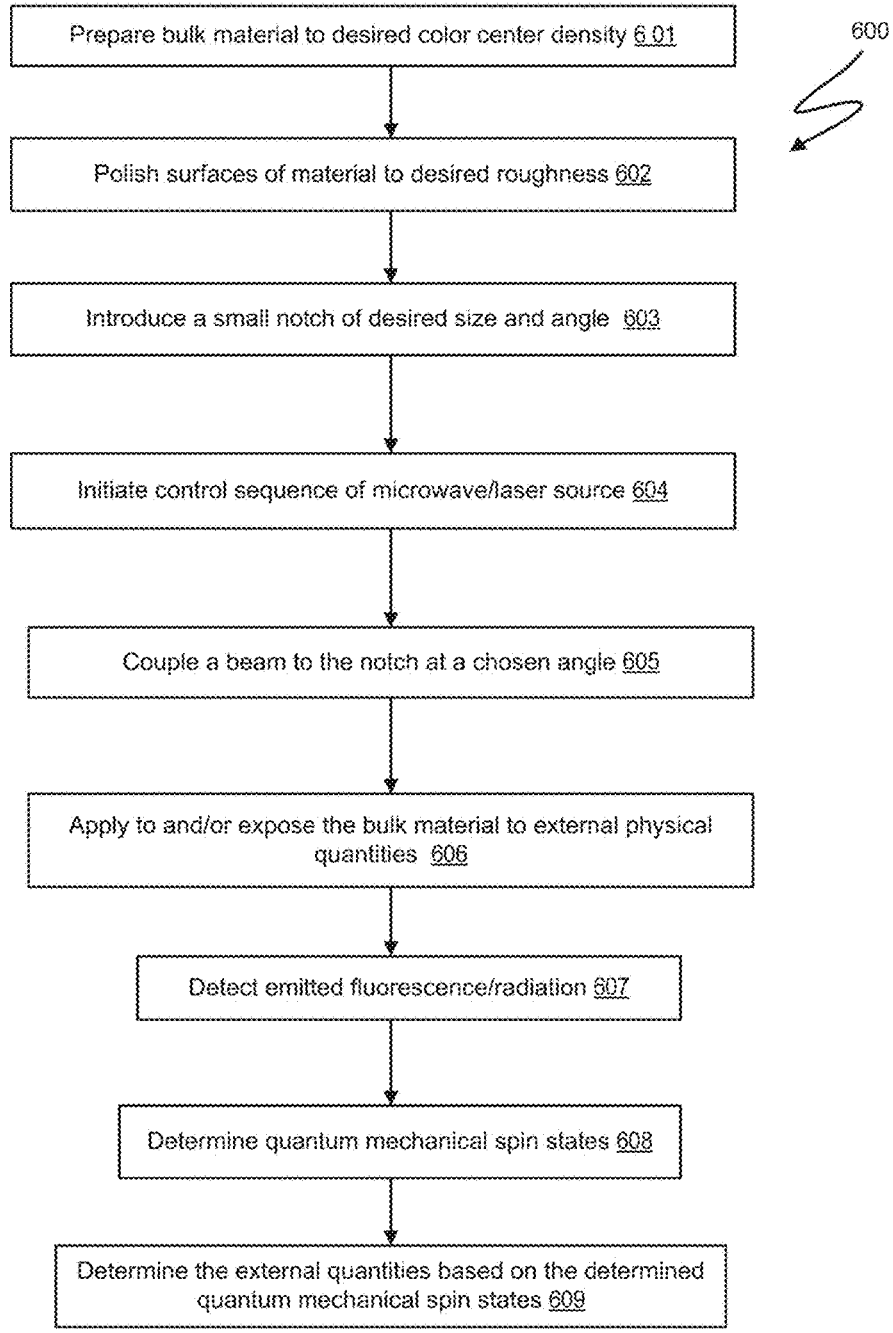
FIG. 6 shows a flow diagram of a process for sensing quantum mechanical spin states associated with a plurality of color centers in a bulk material.

FIG. 6 shows a flow diagram of a process for making and using a sensor that includes a plurality of color centers in a room-temperature bulk crystalline material. The sensor measures the quantum mechanical spin states of the color centers and determines applied pressure, temperature, and/or electromagnetic field strength based on the quantum mechanical state. Such an exemplary method may include, but is not limited to, the following steps, which may be implemented in different orders.

In step 601, a bulk material, such as but not limited to diamond, silicon carbide, etc., crystals, is irradiated and annealed to introduce and/or increase the density of color centers to a desired level. In some embodiments, a low color center density may be desired to maintain the long spin coherence times of the color centers. For example, starting with a ⟨100⟩-oriented, type IIa Chemical Vapor Deposited (CVD) diamond crystal of size 3 mm² by 300 µm, electron-irradiation at 4.5 MeV with a beam current of 20 mA and followed by annealing for 8 hours ramping up to 900 C may result in approximately 0.1 ppm NV centers. In some embodiments, the material may naturally have a desired level of NVs density, and in other embodiments, it may be irradiated further to attain a desired NV density level. In step 602, some or all of the surfaces of the material may be polished to desired roughness (e.g., less than 1 µm of surface roughness) to allow multiple total internal reflections inside the material. For example, all six surfaces of the aforementioned diamond crystal may be polished to a surface roughness of less than 15 nm. Minimal surface roughness would be desirable as surface defects tend to limit LTDW performance. In some embodiments, a prism may also be utilized to achieve total internal reflection.

At step 603, a small facet or notch may be introduced in one corner of the bulk material. As discussed with reference to FIGS. 5A-5H, there may be a need to balance between small facet sizes that allow for longer confinement of light within the bulk material (and hence, for example, more NV centers would be addressed) and large facet sizes that are desirable for improving collection efficiency of signals during transmission measurements. For example, a facet with a size of 500 µm and an angle of 45° may be notched at one corner of the exemplary LTDW to serve as an entrance window for the laser beam, and possibly an exit as well.

At step 604, one may initiate a control sequence of a microwave and/or laser source to manipulate the spin states of the color centers. In some embodiments, the process may be employed at cryogenic temperature, and a control sequence of a laser source may be initiated to manipulate the quantum mechanical spin states of the color centers. In some embodiments, the control sequence may be initiated by a microwave source. In other embodiments, the temperature may be non-cryogenic (e.g., room temperature of about 25° C.), and in such embodiments, a control sequence of a microwave source may be initiated to manipulate the quantum mechanical spin states of the color centers (step 605).

At step 605, an electromagnetic beam (at a laser divergence is about equal to or smaller than the effective numerical aperture of the bulk crystal) may be coupled into the notch of the crystal. The coupling angle and the beam's Rayleigh range may selected to provide a path length inside the material that intersects many color centers. For example, according to numerical simulations, for an LTDW with a notch size of 150 µm and a 35.8° angle of incidence as measured from a line perpendicular to the notch facet, a 31.5 m path length inside the LTDW may be obtained, resulting in most or all NV centers being addressed by the laser beam.

In some implementations, at step 606, an external physical quantity, such as but not limited to magnetic field, temperature, strain, electric field, etc., may be applied to the bulk material. Some or all of these quantities may affect the quantum mechanical spin states of the color centers of the bulk material. As such, to determine the value and other properties of such external physical quantities, at step 609, one may detect and/or measure emitted fluorescence and/or transmissions at step 607, and determine the quantum mechanical spin states from the detection and/or measurements at step 608. For example, as will be discussed below, one may determine shifts in physical quantities such as but not limited to temperature, magnetic field, etc., from fluorescence signals in optically detected magnetic resonances of quantum mechanical spin states of NV centers in a LTDW.

Figure 7A:
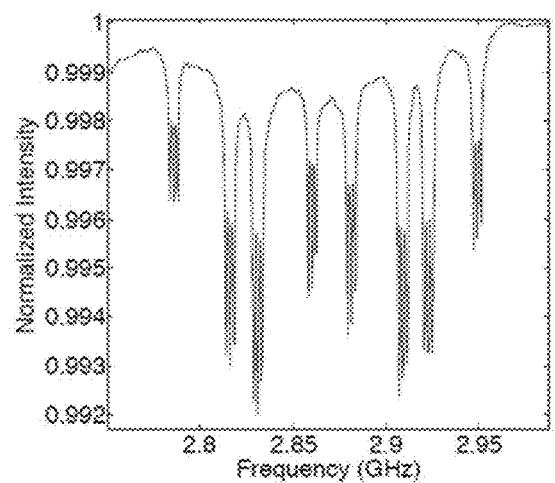
FIGS. 7A and 7B show plots of continuous-wave electron spin resonance signals versus frequency under a static magnetic field in a bulk diamond crystal containing nitrogen vacancies excited using a light-trapping geometry.

FIG. 7A shows normalized intensities of optical transmission measurements of signals emitted by a plurality of NV centers of a diamond crystal in a sensor described in detail with reference to FIG. 2, where the sensor utilizes a 532 nm excitation laser with approximately 1 Watt power. The measurements, shown in the frequency range of about 2.75 GHz to about 3 GHz, are made by using 1042 nm transitions in the singlet states $^1A_1$ and $^1E$ shown in FIG. 1. In this frequency range, the continuous wave electron spin resonance (ESR) fluorescence signal shows a total of eight resonance dips, each of which is further split into triplets with linewidths about 2 MHz from hyperfine coupling to neighboring nuclear spins.

In FIG. 7A, several milliTesla of magnetic field may be used to split out the electron spin resonances of the different orientations. Larger fields would split these resonances out further. The tetragonal diamond lattice allows for four possible nitrogen vacancy defect orientations, creating four sub-ensembles. Without a static applied field, all four orientations are degenerate and there is one resonance. An applied magnetic field causes Zeeman splitting proportional to the projection of the magnetic field direction onto the orientation of each of the four sub-ensembles. By adjusting the orientation of the applied static magnetic field, the splitting for each of the sub-ensembles can be adjusted, and each splitting can be separated and addressed individually. Each of the four orientations splits into two resonances, resulting in a total of eight resonances. Furthermore, hyperfine interactions with nearby nuclear spins cause each of these eight resonances to split into three resonances, for a total of twenty-four resonances.

In FIG. 7A, the eight ESR resonance dips show the splitting of the ESR fluorescence signal into the components of each of the four possible NV orientations in the bulk diamond crystal under a static magnetic field. The static magnetic field is not aligned with any of the NV orientations in the diamond. The projection of the magnetic field onto each of the orientations is different, causing a different splitting. The resonance dips show signal contrast of up to 0.8%, suggesting a high signal-to-noise ratio (about 100) ESR signal from an approximate ensemble of $10^{11}$ NV defect centers. Such signal enhancement facilitates performing quantum spin-sensing measurements without the use of lock-in amplification, allowing experimental detection of magnetic fields with a predicted shot-noise limited sensitivity of ~3 pT. Such a sensor is also capable of detecting changes in resonance frequency of approximately one part in $10^{15}$. Additionally, the contrast can be improved with the implementation of pulsed measurements.

Figure 7B:
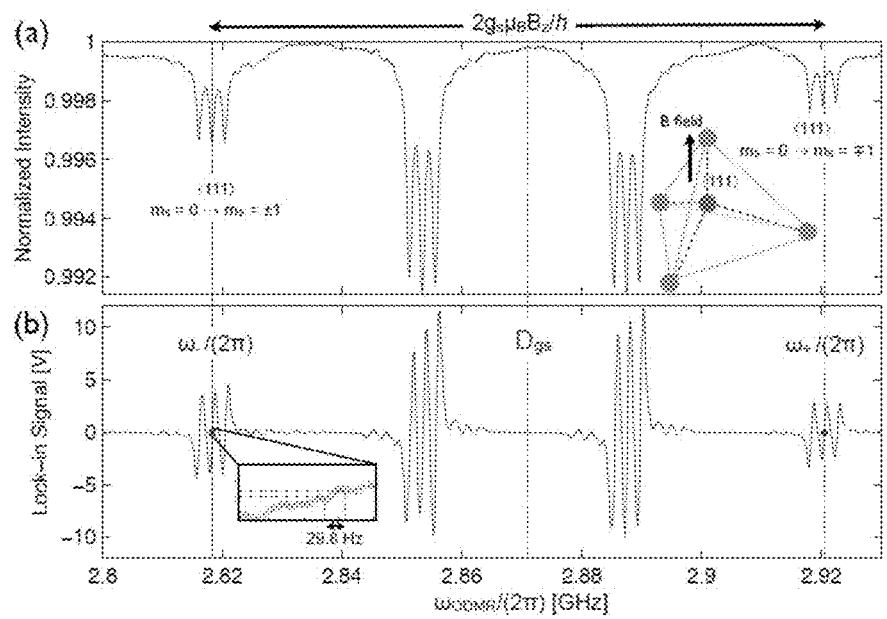

FIG. 7B shows normalized intensities of fluorescence measurements (top) and lock-in signal strength (bottom) for a plurality of NV centers in a bulk diamond. The NVs are illuminated by a 532 nm laser beam with approximately 1 Watt power. The inset in the top panel of FIG. 7B depicts a unit cell of the diamond crystal containing a nitrogen atom in the middle taking the place of a vacancy from a missing carbon atom, and surrounded by four carbon atoms in a tetrahedral crystal structure. There are four possible orientations for the vacancy, defining the four sub-ensembles of NV centers.

A static (or slowly varying) magnetic field may be applied along a single $\langle 111 \rangle$ crystal axis of the LTDW using Helmholtz coils or any other suitable magnetic field source. For example, by using a calibrated rotation matrix between the tetragonal crystal axes and Cartesian Helmholtz coils, a static magnetic field of about 2.5 mT may be applied along the $\langle 111 \rangle$ diamond crystal axis. The sub-ensemble of NVs whose quantization axis is aligned with the magnetic field direction (in this case, the $\langle 111 \rangle$ direction as shown in the inset) may show the greatest splitting, while due to equal magnetic field projection along each axis, the transitions of the three remaining NV orientations have a degenerate frequency splitting giving three times the contrast as the $\langle 111 \rangle$ sub-ensemble. The amplitude of this resonance may also be proportionally larger due to the larger population. Each transition/resonance appears as a Lorentzian triplet with a full width half max of about 1.2 MHz spaced by about 2.1 MHz due to hyperfine coupling to nearby nuclear spins.

The lock-in signals identify the locations of the resonances the ensembles of NV centers in the optical transmission measurements. The steep slope of these lock-in signals result in the centers of the resonance having highest sensitivities to frequency shifts. The scale factor (V/Hz) may be provided by a linear fit around the intersection points between the vertical dashed lines and the lock-in signal at frequencies of about 2.82 GHz and 2.92 GHz. The inset in the bottom panel of FIG. 7B shows detail of the noise on this curve around the left-most intersection point. For example, a signal from a lock-in amplifier, measured in volts, may be translated into a minimum resolvable frequency shift, measured in Hertz, using the slope of the line and the noise in the signal.

Although FIG. 7B shows comparable signal contrast of up to 0.8% to that of FIG. 7A, the larger number of NV defect centers results in a high signal-to-noise ratio of about $10^5$ for one second of averaging. Frequency modulation of the RF source in combination with lock-in detection may further increase SNR and also resolution. Modulation of the signal using the lock-in amplifier allows one to filter low frequency noise.

Figure 8A:
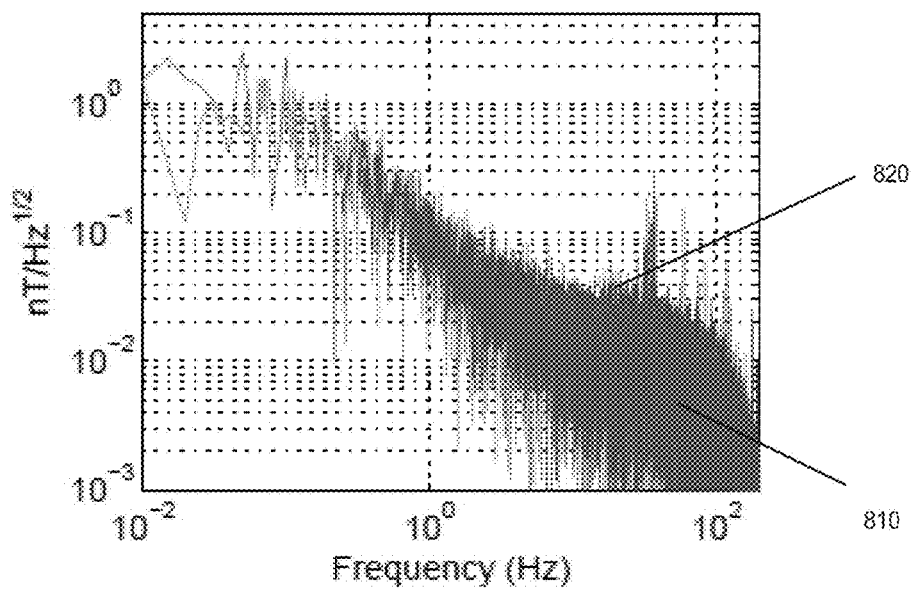
FIG. 8A shows a plot of lock-in amplifier noise versus frequency of an exemplary light-trapping diamond waveguide system.

FIG. 8A shows plots of lock-in amplifier noise versus frequency of the LTDW described in the set-up with reference to FIG. 7B. The fast Fourier transform plots 810 and 820 are for the resonances of $\langle 111 \rangle$ orientation sub-ensembles of NV centers in LTDW at frequencies of 2.82 GHz and 2.92 GHz, respectively. The plots show the magnetic field sensitivities of these two resonances. For example, at 1 Hz, both transitions/resonances of the $\langle 111 \rangle$ orientation sub-ensemble are sensitive to less than 1 nT/√Hz, demonstrating increased sensitivity to magnetic fields at low frequencies (e.g., in 1 Hz range).

Figure 8B:
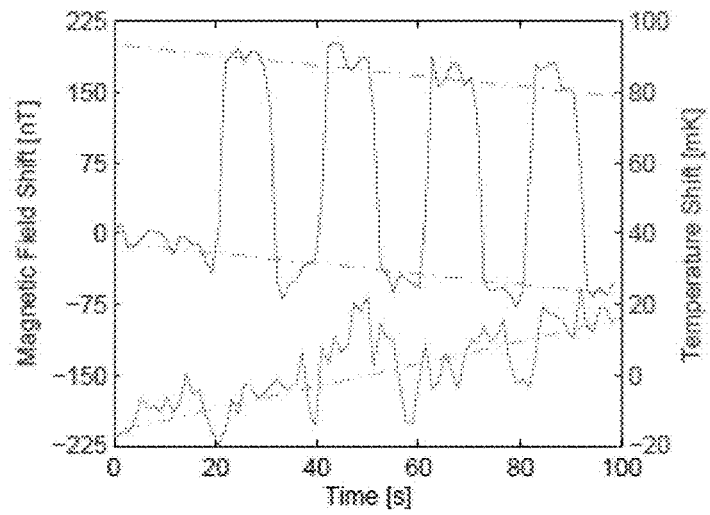
FIG. 8B shows magnetic field (upper curve) and temperature (lower curve) versus time at resonances.

FIG. 8B shows plots of the sum (lower trace) and difference (upper trace) of the error signals from 2.82 GHz and 2.92 GHz resonances versus time for the setup used in FIGS. 7B and 8A. As described below, the sum corresponds to magnetic field shift while the difference corresponds to temperature shift, separating out magnetic field and temperature effects from the measured resonance measurements. Over about a time period of about 100 seconds, the magnetic field shift oscillates with a period of about 20 s (0.1 Hz square wave perturbation with an amplitude of 200 nT along the $\langle 111 \rangle$ axis) with a downward drift of approximately 50 nT in the same time period. The temperature shift shows a steady, generally linear but noisy incline during the 100-second time period, with a total of 40 mK temperature shift, which may be attributed to geomagnetic fluctuations. The separation of magnetic field and temperature effects follows from the separate effects these quantities have on the quantum mechanical spin states of the NV centers, as discussed below.

By sequentially monitoring both transitions/resonances at 2.82 GHz and 2.92 GHz, one may analyze the effectively orthogonal measurements of the splitting of $m_s=\pm 1$ spin singlet states shown in FIG. 1 as well as the shift of the zero field splitting resonance. For example, monitoring the central hyperfine resonance on the lower frequency side of the $\langle 111 \rangle$ orientation makes it possible to resolve shifts of 29.8 Hz after one second of averaging, corresponding to a 1.06 nT shift in magnetic field or a 400 µK shift in temperature.

As discussed with reference to FIG. 1, the energy of the low energy states comprises the term $D_{gs}S_z^2$ where $D_{gs}$ is the ground state crystal field splitting, and $S_z$ is the spin projection onto the z axis. Effects that are proportional to $S_z^2$ in the energy term which comprise temperature and/or strain, may cause both resonances to shift in the same direction in frequency. In some embodiments, the intrinsic strain across the sample may not change over the course of the measurement, and the shift due to strain may be ascribed to external pressure/strain. Magnetic fields, which are proportional to $S_z$, may cause field-induced splitting to increase or decrease, allowing these effects to be separated to first order.

The relative and absolute frequency shifts may be monitored on a single lock-in amplifier by alternating between $m_s=\pm 1$ frequencies in 250 ms steps. Using an amplifier with an acquisition time of 50 ms gives 200 ms of data at each time step. For a 1-second integration time, 4 points may then be averaged, and the difference and sum of the sequential points give the magnetic field shift and temperature shift, respectively, which follows from the effects of magnetic field to the energy of the quantum mechanical states being first order in $S_z$ compared to second order for quantities such as but not limited to temperature, strain, etc.

Figure 9:
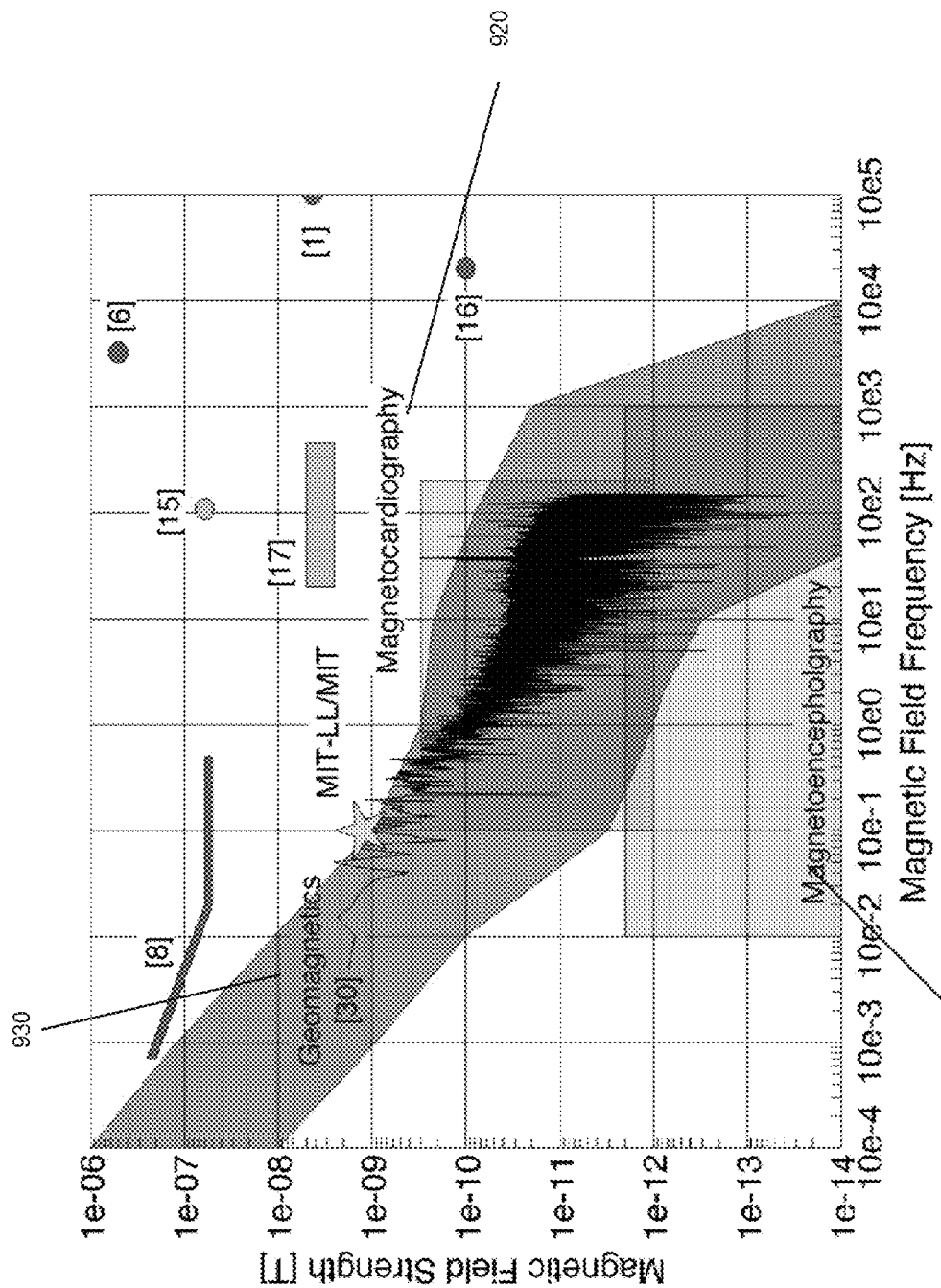
FIG. 9 shows comparison of the performances of an exemplary implementation of a light-trapping diamond waveguide to other diamond-based magnetic-field sensors.

FIG. 9 shows a comparison of different diamond-based sensors. It shows the sensitivity requirements of several target applications, such as but not limited to magnetocardiography 910, magnetoencephalography 920, geomagnetic fluctuations 930, etc., in combination with the sensitivity of the LTDW and that of other NV-based systems. In a frequency range not accessible by dynamical decoupling techniques, exemplary LTDW sensors may attain magnetic field sensitivity of approximately 1 nT/√Hz in the range of 0.1 Hz to 10 Hz (e.g., as shown in FIG. 8A) and a thermal sensitivity of approximately 400 μK/√Hz. Further, spin projection limits of device sensitivity may be determined at approximately 0.36 fT/√Hz and 139 pK/√Hz for magnetic field and thermal sensitivities, respectively.

For example, the sensor disclosed herein may exhibit unprecedented sensitivity to temperature and magnetic field shifts using a CW excitation scheme in ensembles of NV centers in diamond, particularly at low frequencies (e.g., about $10^{-1}$ to about 10 Hz), which may be preferable for object detection and magnetocardiography 910 applications. In contrast, other diamond-based magnetometer systems with comparable sensitivity detect only high frequency magnetic fields in the 100 Hz to low kHz range. This high frequency sensitivity may not be useful for the majority of magnetic field sensing applications including biological applications such as magnetoencephalography 920 and magnetocardiography 910, object detection, and the monitoring of geomagnetic fluctuations 930, which may occur in the $10^{-4}$ to 10 Hz range. In some embodiments, the high SNR of the LTDW allows modulation between the low and high frequency resonance transitions of one NV center orientation for separating effects of strain and magnetic field at short integration times beyond the capabilities of confocal microscopy.

Increasing collection efficiency with the addition of more photodetectors, improving the homogeneity of the RF excitation, improved surface smoothness, and further optimization of the density of NV centers may improve the performance of the device. For example, by efficiently trapping excitation photons and achieving high fluorescence collection, an exemplary sensor is fully compatible with low NV density diamond samples that allow for extremely long coherence times. In some embodiments, samples with very high color center densities may show poor spin coherence properties, and hence may show reduced performance as sensors compared to samples with optimized color center densities. In some embodiments, the sensors may have low concentration of defect centers, including as low as a single defect center emitter. In some embodiments, an optimized defect center concentration of greater than 1 part per billion may be desired for sensing applications.

Collection efficiency can also be increased with the addition of prisms or mirrors directing the fluorescence from non-adjacent sides of the diamond to the detector, or with the addition of multiple photodetectors. Improving the homogeneity of the RF excitation may increase contrast for higher SNR. Improvements in surface defects and polishing may allow for less restricted green state preparation in the current geometry. Other TIR geometries such as chaotic excitation (e.g., excitations from quasi-chaotic mode) can also be used for NV excitation. Further, this technique could be extended to be used for transmission measurements and direct IR absorption techniques.

Exemplary devices may also be used for other applications, including any application involving a long optical path length within the sample (e.g., electromagnetically induced transparency experiments and optical quantum memories). The dynamic ranges that the measurements can occur may be quite large, with upper limits set by physical quantity values leading to the breakdown of the material itself. The electron spin de-phasing time of the color centers may determine the limits, if any, of the sensitivities of the measurements. Since the NVs have not saturated at the maximum laser power discussed herein, these structures could be fabricated on the scale of tens to hundreds of microns, which would also allow increased spatial resolution.

Further inventive embodiments comprise the determination of the homogeneity of the zero field splitting and the effects of strain across bulk diamond samples, as well as the effect these will have on pulsed measurements with this device. In addition, the sensing device disclosed herein may be implemented in other materials with defects centers besides diamond, such as silicon carbide, etc. As another example, the device disclosed herein can be used to address nuclear spins with long lived spin coherence. Further, the device may generally perform frequency-modulated continuous-wave optically detected magnetic resonance.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of designing and making the coupling structures and diffractive optical elements disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (e.g., of designing and making the coupling structures and diffractive optical elements disclosed above) outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method for sensing quantum mechanical spin states associated with a plurality of color centers in a room-temperature bulk crystalline material, the method comprising:
    (A) coupling an electromagnetic beam into the room-temperature bulk crystalline material along a propagation path within the room-temperature bulk crystalline material so as to cause the electromagnetic beam to excite the plurality of color centers, the propagation path including a plurality of reflections off surfaces of the room-temperature bulk crystalline material, the plurality of reflections being at one or more angles with respect to the surfaces of the room-temperature bulk crystalline material;
    (B) detecting, with at least one detector, electromagnetic radiation emitted and/or transmitted by the plurality of color centers in response to excitation of the plurality of color centers in (A); and
    (C) determining, from the electromagnetic radiation detected in (B), the quantum mechanical spin states of the plurality of color centers.

2. The method of claim 1, wherein (A) comprises coupling the electromagnetic beam into the room-temperature bulk crystalline material via a facet of the room-temperature bulk crystalline material.

3. The method of claim 2, wherein (A) further comprises matching a divergence of the electromagnetic beam to a numerical aperture of the facet.

4. The method of claim 1, wherein (A) comprises coupling the electromagnetic beam into the room-temperature bulk crystalline material so as to cause at least a portion of the electromagnetic beam to totally internally reflect off at least one surface of the room-temperature bulk crystalline material.

5. The method of claim 1, wherein (A) comprises coupling the electromagnetic beam to a chaotic mode of the room-temperature bulk crystalline material.

6. The method of claim 1, wherein (A) comprises coupling the electromagnetic beam to a non-chaotic mode of the room-temperature bulk crystalline material.

7. The method of claim 1, wherein (A) comprises modulating the electromagnetic beam.

8. The method of claim 1, further comprising:
    (D) exciting the plurality of color centers with microwave radiation so as to cause the color centers to emit and/or transmit the electromagnetic radiation in (B).

9. The method of claim 1, further comprising:
    (E) applying a strain, a temperature, and/or an electromagnetic field to the room-temperature bulk crystalline material; and
    (F) determining the strain, the temperature, and/or an amplitude of the electromagnetic field applied to the room-temperature bulk crystalline material in (E) based on the quantum mechanical spin states determined in (C).

10. An apparatus comprising:
    a room-temperature bulk crystalline material comprising a plurality of color centers;
    a source, in electromagnetic communication with the room-temperature bulk crystalline material, to couple an electromagnetic beam into the room-temperature bulk crystalline material along a propagation path within the room-temperature bulk crystalline material so as to cause the electromagnetic beam to excite the plurality of color centers, the propagation path including a plurality of reflections off surfaces of the room-temperature bulk crystalline material, the plurality of reflections being at one or more angles with respect to the surfaces of the room-temperature bulk crystalline material; and
    at least one detector, in electromagnetic communication with the room-temperature bulk crystalline material, to detect electromagnetic radiation emitted and/or transmitted by the plurality of color centers in response to excitation of the plurality of color centers by the electromagnetic beam.

11. The apparatus of claim 10, wherein the room-temperature bulk crystalline material comprises diamond and the plurality of color centers comprises a plurality of nitrogen vacancies.

12. The apparatus of claim 10, wherein:
    the room-temperature bulk crystalline material defines a facet, and
    the source is configured to couple the electromagnetic beam into the room-temperature bulk crystalline material via the facet.

13. The apparatus of claim 12, further comprising:
at least one beam-shaping element, in electromagnetic communication with the source and the facet, to match a divergence of the electromagnetic beam to a numerical aperture of the facet.

14. The apparatus of claim 10, wherein the source is configured to couple the electromagnetic beam into the room-temperature bulk crystalline material so as to cause at least a portion of the electromagnetic beam to totally internally reflect off at least one surface of the room-temperature bulk crystalline material.

15. The apparatus of claim 10, wherein the source is configured to couple the electromagnetic beam to a chaotic mode of the room-temperature bulk crystalline material.

16. The apparatus of claim 10, wherein the source is configured to couple the electromagnetic beam to a non-chaotic mode of the room-temperature bulk crystalline material.

17. The apparatus of claim 10, further comprising:
a modulator, in electromagnetic communication with the source, to modulate the electromagnetic beam.

18. The apparatus of claim 10, further comprising:
a microwave source, in electromagnetic communication with the room-temperature bulk crystalline material, to excite the plurality of color centers with microwave radiation so as to cause the color centers to emit and/or transmit the electromagnetic radiation in (B).

19. The apparatus of claim 10, further comprising:
a processor, operably coupled to the at least one detector, to determine the quantum mechanical spin states of the plurality of color centers based at least in part on the electromagnetic radiation detected by the at least one detector.

20. The apparatus of claim 10, wherein the processor is configured to determine a strain, a temperature, and/or an electromagnetic field applied to the room-temperature bulk crystalline material based at least in part on the quantum mechanical spin states of the plurality of color centers.

21. A sensor comprising:
a diamond defining a plurality of polished surfaces and comprising a plurality of nitrogen vacancies, the plurality of nitrogen vacancies having a first energy level and a second energy level;
a laser, in optical communication with the diamond, to couple a laser beam into the diamond so as to cause the laser beam to excite at least a portion of the plurality of color centers via propagation along a path within the diamond, the path within the diamond comprising at least one total internal reflection from at least one polished surface in the plurality of polished surfaces; and
at least one detector, in optical communication with the diamond, to detect a change in optical radiation emitted and/or transmitted by the at least a portion of the plurality of color centers excited by the laser beam,
wherein the change in optical radiation is proportional to a change in temperature, pressure, and/or electromagnetic field applied to the diamond.

22. The method of claim 1, wherein (A) comprises focusing the electromagnetic beam to a point at an end of the propagation path.

23. The method of claim 1, wherein the propagation path is at least 100 times longer than a length of the room-temperature bulk crystalline material.

24. The method of claim 1, wherein the propagation path is about 100,000 times longer than a length of the room-temperature bulk crystalline material.

25. The method of claim 1, wherein the propagation path has a length of about 30 meters.

* * * * *